United States Patent
Zhang et al.

(10) Patent No.: US 7,988,666 B2
(45) Date of Patent: Aug. 2, 2011

(54) BROADBAND INFRARED HEATING OF MEDICAL FLUIDS

(75) Inventors: Wenwei Zhang, Bellshill (GB); Frank Turnbull, Larkhall (GB); Martin Faulks, Bucks (GB)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 12/535,045

(22) Filed: Aug. 4, 2009

(65) Prior Publication Data

US 2011/0034866 A1    Feb. 10, 2011

(51) Int. Cl.
A61F 7/12    (2006.01)

(52) U.S. Cl. .............. 604/113; 604/291; 604/29

(58) Field of Classification Search ........... 604/29, 604/31, 131, 113, 291
See application file for complete search history.

(56) References Cited

U.S. PATENT DOCUMENTS

| | | | |
|---|---|---|---|
| 5,350,357 A | 9/1994 | Kamen et al. | |
| 5,493,629 A | 2/1996 | Stange | |
| 5,498,338 A * | 3/1996 | Kruger et al. ........... | 210/641 |
| 5,634,896 A | 6/1997 | Bryant et al. | |
| 5,643,201 A * | 7/1997 | Peabody et al. ........... | 604/31 |
| 5,938,634 A | 8/1999 | Packard | |
| 5,989,423 A | 11/1999 | Kamen et al. | |
| 6,429,294 B1 | 8/2002 | Masuda et al. | |
| 6,595,948 B2 | 7/2003 | Suzuki et al. | |
| 6,613,095 B1 | 9/2003 | Levin | |
| 6,656,227 B2 | 12/2003 | Levin | |
| 7,153,285 B2 | 12/2006 | Lauman et al. | |
| D556,909 S | 12/2007 | Reihanifam et al. | |
| 7,458,951 B2 | 12/2008 | Lauman et al. | |
| 7,809,254 B2 | 10/2010 | Lindsay et al. | |
| 2002/0045851 A1 | 4/2002 | Suzuki et al. | |
| 2003/0135250 A1 | 7/2003 | Lauman et al. | |
| 2003/0216689 A1 | 11/2003 | Bouhuijs et al. | |
| 2003/0220607 A1 | 11/2003 | Busby et al. | |
| 2006/0195064 A1 | 8/2006 | Plahey et al. | |
| 2007/0112297 A1 | 5/2007 | Plahey et al. | |
| 2008/0015492 A1 | 1/2008 | Biesel | |
| 2008/0097283 A1 | 4/2008 | Plahey | |
| 2009/0010627 A1 | 1/2009 | Lindsay et al. | |
| 2009/0012450 A1 * | 1/2009 | Shah et al. ........... | 604/29 |
| 2009/0012655 A1 | 1/2009 | Kienman et al. | |

FOREIGN PATENT DOCUMENTS

| WO | 2008/027967 A1 | 3/2008 |
|---|---|---|
| WO | 2008027971 A2 | 3/2008 |

* cited by examiner

*Primary Examiner* — Theodore J Stigell
*Assistant Examiner* — Deanna K Hall
(74) *Attorney, Agent, or Firm* — Shumaker & Sieffert, P.A.

(57) ABSTRACT

A system for heating a medical fluid includes a container including a fluid path including an inlet side and an outlet side. A broadband infrared radiation source including a power supply is coupled to a broadband emitter for emitting infrared radiation. The broadband emitter provides a focal location within the fluid path to heat the medical fluid to generate a heated medical fluid. A flow turbulence enhancing structure mixes the heated medical fluid to reduce temperature gradients therein. A fluid detector senses a presence of the medical fluid in the fluid path and generates a fluid sensing signal. A controller is coupled to receive the fluid sensing signal and has an output coupled to the power supply for controlling a power output of the power supply based on the fluid sensing signal indicating a presence of the medical fluid in the container.

22 Claims, 7 Drawing Sheets

BROADBAND INFRARED HEATING OF MEDICAL FLUIDS

FIELD

Disclosed embodiments relate to non-contact infrared heating of medical fluids.

BACKGROUND

There are a variety of medical applications that involve heating a medical fluid to a temperature that is at, or is near, the body temperature of a patient. In such applications, the heating is performed in a non-contact manner to prevent adding contamination. For example, blood transfusion is one common medical application that requires controlled heating of the blood. Another medical application is peritoneal dialysis, where wastes such as urea and potassium are removed from the blood, as well as excess fluid, when the kidneys are incapable of performing this function (i.e. renal failure). Because the patient can only comfortably adopt the medical fluid within a tight temperature range that is similar to that of the human body, the medical fluid is heated in a fairly narrow range prior to infusion to the patient to avoid discomfort or harming of the patient.

SUMMARY

This Summary is provided to comply with 37 C.F.R. §1.73, presenting a summary for disclosed embodiments and their equivalents to briefly indicate the nature and substance disclosed in this application. It is submitted with the understanding that it will not be used to interpret or limit the scope or meaning of the claims.

Disclosed embodiments include systems for non-contact heating of medical fluids that comprise a container having at least one inlet for receiving the medical fluid and at least one outlet for delivering the medical fluid, and a fluid path within the container having an inlet side coupled to the inlet and an outlet side coupled to the outlet. At least one broadband infrared radiation source comprising a power supply is coupled to a broadband emitter for emitting infrared radiation. The broadband infrared radiation source provides a focus location within the fluid path to heat the medical fluid to provide a heated medical fluid.

The Inventor has recognized that broadband infrared radiation sources provide a small focus location, typically being about 5 mm for liquid targets, and as a result concentrates the heating of the medical fluid into a small zone relative to the overall volume of the medical fluid. The Inventor has also discovered that the temperature of the heated medical fluid is generally highly non-uniform, and can vary $\geq 10°$ C., such as up to about $50°$ C., across a cross-sectional area of the flowing medical fluid. In response to this discovery, a flow turbulence enhancing structure for fluid mixing is added to enhance mixing of the flowing heated medical fluid to improve its temperature uniformity before the heated medical fluid is delivered to the patient. The flow turbulence enhancing structure can mix the heated medical fluid in the fluid path within the container and can be embodied as either a passive or active flow turbulence enhancing structure.

Systems disclosed herein can also include at least one fluid detector for sensing a presence of the medical fluid in the fluid path and for generating a fluid sensing signal. In this embodiment, a controller having an input is coupled to receive the fluid sensing signal and provides an output that is coupled to the power supply. The controller can control a power output of the power supply so that the broadband infrared radiation source is switched on only when the fluid sensing signal indicates the medical fluid is present in the container.

In one disclosed embodiment the broadband infrared radiation source is placed (e.g., mounted) within a dialysis machine which includes a housing. In this embodiment, the container comprises a cartridge positioned within the housing and the inlet comprises a cartridge inlet and the outlet comprises a cartridge outlet, wherein the cartridge comprises a reservoir in the fluid path. The broadband infrared radiation source is positioned in the region between the fluid path and the housing. In one embodiment, the medical fluid can be heated while in the reservoir.

In another disclosed embodiment the system for heating medical fluid is in the form of a dedicated container for heating the medical fluid, and is thus separate from the dialysis machine. In this embodiment the dedicated container can be connected to the cartridge inlet or cartridge outlet of the dialysis machine. This embodiment allows adding the system for heating medical fluid to an existing dialysis machine design without modifying the design of the cartridge.

Another disclosed embodiment comprises a method for heating a medical fluid. The method comprises flowing the medical fluid into a fluid path within a container having an inlet and an outlet, heating the medical fluid by directing broadband infrared radiation having a focus location within the fluid path to provide a heated medical fluid, and mixing the heated medical fluid using flow turbulence in the fluid path or proximate to the outlet for increasing a temperature uniformity of the heated medical fluid. The method can also comprise sensing a presence of the medical fluid or the heated medical fluid in the fluid path and for generating a fluid sensing signal, and controlling the heating by emitting the broadband infrared radiation only while the fluid sensing signal indicates the medical fluid is present in the container. Fluid sensing can avoid melting or burning of the container (e.g., cartridge) during dry conditions.

DETAILED DESCRIPTION

Figure 1A:
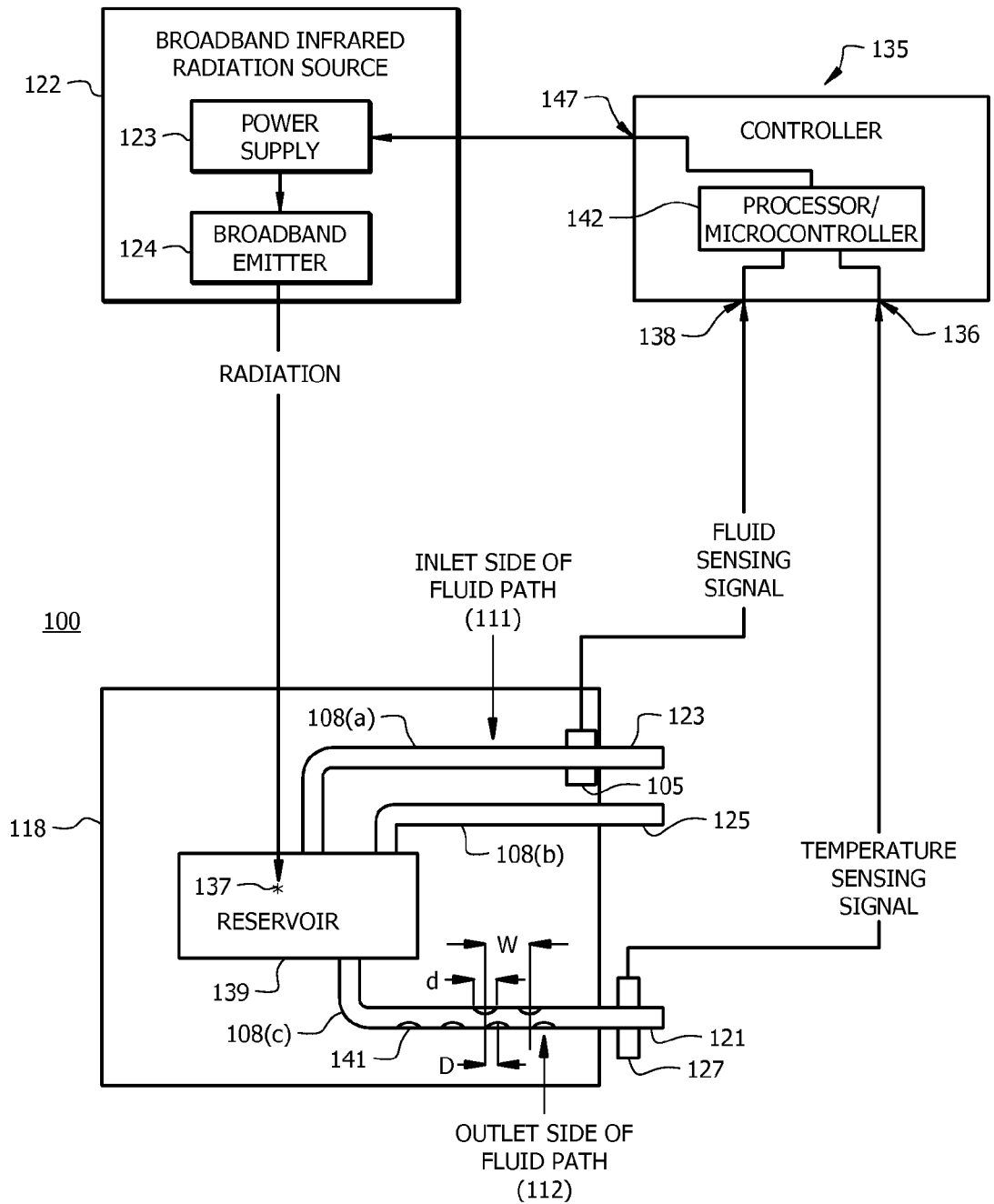
FIG. 1A illustrates a schematic of a system for heating a medical fluid comprising a flow turbulence enhancing structure comprising a plurality of flow obstacles for mixing the heated medical fluid and at least one fluid detector for sensing the medical fluid and shutting off the radiation source when an insufficient flow is detected, according to a disclosed embodiment.

The embodiments disclosed in this application are described with reference to the attached figures, wherein like reference numerals are used throughout the figures to designate similar or equivalent elements. The figures are not drawn to scale and they are provided merely to illustrate the disclosed embodiments. Several disclosed aspects are described below with reference to example applications for illustration. It should be understood that numerous specific details, relationships, and methods are set forth to provide a full understanding of the disclosed embodiments. One having ordinary skill in the relevant art, however, will readily recognize that the disclosed embodiments can be practiced without one or more of the specific details or with other methods. In other instances, well-known structures or operations are not shown in detail to avoid obscuring disclosed embodiments. The disclosed embodiments and their equivalents are not limited by the illustrated ordering of acts or events, as some acts may occur in different orders and/or concurrently with other acts or events. Furthermore, not all illustrated acts or events are required to implement a methodology in accordance with the disclosed embodiments.

FIG. 1A illustrates a schematic of a system 100 for heating a medical fluid comprising a container 118 having at least one inlet, shown as inlets 123 and 125, for receiving the medical fluid and at least one outlet 121 for delivering the medical fluid following heating, such as to a medical patient (not shown). A fluid path referred to collectively as 108 is within the container 118 having an inlet side 111 comprising fluid path portions 108(a) and 108(b) coupled to inlets 123 and 125 respectively, and an outlet side 112 having a fluid path portion 108(c) coupled to the outlet 121. At least one broadband infrared radiation source 122 comprising a power supply 123 is coupled to a broadband emitter 124 for emitting infrared radiation. The broadband emitter 124 is positioned appropriately and includes a structure to provide a focal location 137 within the fluid path 108 to heat the medical fluid (e.g., a reflector at the back of the broadband emitter 124), with the focal location 137 shown in FIG. 1A being within the reservoir 139. Alternatively, although not shown in FIG. 1A, the focal location 137 can be within the fluid path portion 108(c).

As compared to a conventional LED or laser source, a broadband emitter 124 embodied as a blackbody infrared source (e.g., tungsten coil) is a broadband source with a peak wavelength and broad spectrum ranging from visible light to the mid-infrared range (50 μm). A typical blackbody emission spectrum has its peak wavelength at about 1.9 μm and the overall wavelength range is from UV band to far infrared band. However, its half-power wavelength range is from 1.2 μm to 3.5 μm, with about 75% of its total optical power emitted embedded in this wavelength range. As known in the art, the peak wavelength of a blackbody source can be tuned longer and shorter with operating temperature (i.e. shorter wavelength for higher temperature), while the operating temperature of blackbody source can be changed by selection of the material.

Conventional peritoneal dialysis fluids comprise glucose and other contents dissolved in water, while blood is also primarily water. Technically, being primarily water, the dialysis fluid or blood can be treated as water for absorption purposes. According to the absorption spectrum of water, water has significant absorption rate when wavelength of the radiation is >1.4 μm.

In one disclosed embodiment the broadband infrared radiation source 122 provides a peak wavelength≧2 microns, and the material comprising the container 118 provides ≧80% average transmission for a 0.5 mm thickness in a wavelength range from 2 to 4 μm. For example, the container material can comprise polyethylene or polymethyl methacrylate (PMMA). In another disclosed embodiment, the broadband infrared radiation source 122 provides a peak wavelength≧3 microns and the container material provides ≧80% average transmission for a 0.5 mm thickness in a wavelength range from 2 to 5 μm.

A flow turbulence enhancing structure comprising a plurality of flow obstacles 141 is shown in FIG. 1A protruding from the inner walls in fluid path portion 108(c). The plurality of flow obstacles 141 are thus positioned downstream from the focal location 137 for mixing the heated medical fluid to reduce temperature gradients therein prior to delivery to the patient.

The plurality of flow obstacles 141 protrude from inner walls of the fluid path to provide an obstruction of between 20% and 50% of the cross sectional area of the fluid path portion having the flow obstacles 141, for an exemplary length of the fluid path portion having the flow obstacles 141 of 30 mm. Flow obstacles 141 too large (e.g., substantially >50% obstruction) may result in a build up of back pressure in the fluid path. The size of the flow obstacles 141 can be based on the expected temperate rise of the medical fluid provided by system 100 in a given application and to a lesser extent the length of the fluid path portion 108(c) having the flow obstacles 141.

For example, assuming the target temperate for the heated medical fluid is around 39° C., the temperature rise will generally depend on the room temperature which generally sets the temperature of the medical fluid before heating. For a 10 to 12° C. temperature rise and length of the fluid path portion having the flow obstacles 141 of 30 mm, 20% has been found to be generally sufficient to provide mixing, while for a 26-28° C. temperature rise again for a length of the fluid path portion having the flow obstacles 141 of 30 mm, 45 to 50% is generally sufficient to provide the desired mixing. As the length of the fluid path portion having the flow obstacles 141 increases from 30 mm, the % obstruction can generally be decreased, while if the length of the fluid path portion having the flow obstacles 141 decreases from 30 mm, the % obstruction can generally be increased to provide the desired mixing.

FIG. 1A also shows a parameters (d) that can be used characterize a dimension of the flow obstacles 141 and two parameters (W and D) that can be used to characterize the spacing between adjacent flow obstacles 141. In some experiments performed by the Inventors, the best mixing results were typically obtained when the flow obstacles 141 were arranged so that the following approximate relations were provided, D=3d and W=6d. However, other flow obstacles 141 arrangements/relations can be used. As a general rule, to obtain effective mixing, the spacings between the flow obstacles 141 (D and W) are made larger as the protrusion of the flow obstacles 141 is increased, and the spacing between flow obstacles 141 (D and W) are made smaller as the protrusion of the flow obstacles 141 is decreased.

The plurality of flow obstacles 141 can comprise small bars. In one embodiment the plurality of flow obstacles 141 can be molded along the fluid path portion 108(*c*) of container 118 during manufacturing. (see FIGS. 6A and 6B described below). In addition, during manufacturing, the surface roughness of fluid path portion 108(*c*) can be made very large, such as an arithmetic average roughness (Ra) of about 100 μm in one particular embodiment. As described relative to FIG. 1B, as an alternative to a passive flow turbulence enhancing structure, the flow turbulence enhancing structure can comprise an active structure such as ultrasonic wave generator for generating vibrational waves in the heated medical fluid to enhance fluid mixing to reduce the temperature gradient in the heated medical fluid. In yet another embodiment, the flow turbulence enhancing structure can include both passive and active elements.

System 100 is shown comprising a temperature sensor 127 for measuring a temperature of the heated medical fluid and for generating a temperature sensing signal. The temperature sensor 127 can comprise a contact sensor such as a thermistor, resistance temperature detector (RTD), or temperature sensing diode or a non-contact temperature sensor such as an IR sensor. The temperature sensing signal is communicably coupled (e.g., wire, optically or over the air) to a controller 135 shown comprising a processor or microcontroller 142, shown in FIG. 1A being coupled to a first input 136 of controller 135, wherein the controller 135 controls the power output of power supply 123 based on the temperature sensing signal to maintain the heated medical fluid in a predetermined temperature range. When the temperature sensor 127 is a contact sensor it is generally attached to the outlet 121 as shown in FIG. 1A, such as via a thermally conductive adhesive (e.g., Ag-filled epoxy). For non-contact embodiments, such as using IR sensors, temperature sensor 127 is spaced apart from the outlet 121, such as a distance of about 6 to 14 cm.

To avoid directing too much energy from the broadband infrared radiation source 124 to the container 118 without sufficient fluid being in the container, at least one fluid detector 105 can be positioned near the inlet 123 for sensing a presence of the medical fluid in the fluid path 108 and for generating a fluid sensing signal. The fluid detector 105 can comprise a variety of different detector types, such as ultrasonic, optical transmissive, or optical reflective-based fluid-based detectors. Although the fluid detector 105 is shown only at inlet 123 in FIG. 1A, fluid detectors can be at any or all of the plurality of inlets.

Controller 135 has an a second input 138 that is coupled to receive the fluid sensing signal and an output 147 that is coupled to the power supply 123. The controller 135 can be operable for controlling a power output of the power supply 122 so that the broadband infrared radiation source 124 is switched on only when the fluid sensing signal indicates the medical fluid is present in the container 118, or is present in a minimum amount.

Figure 1B:
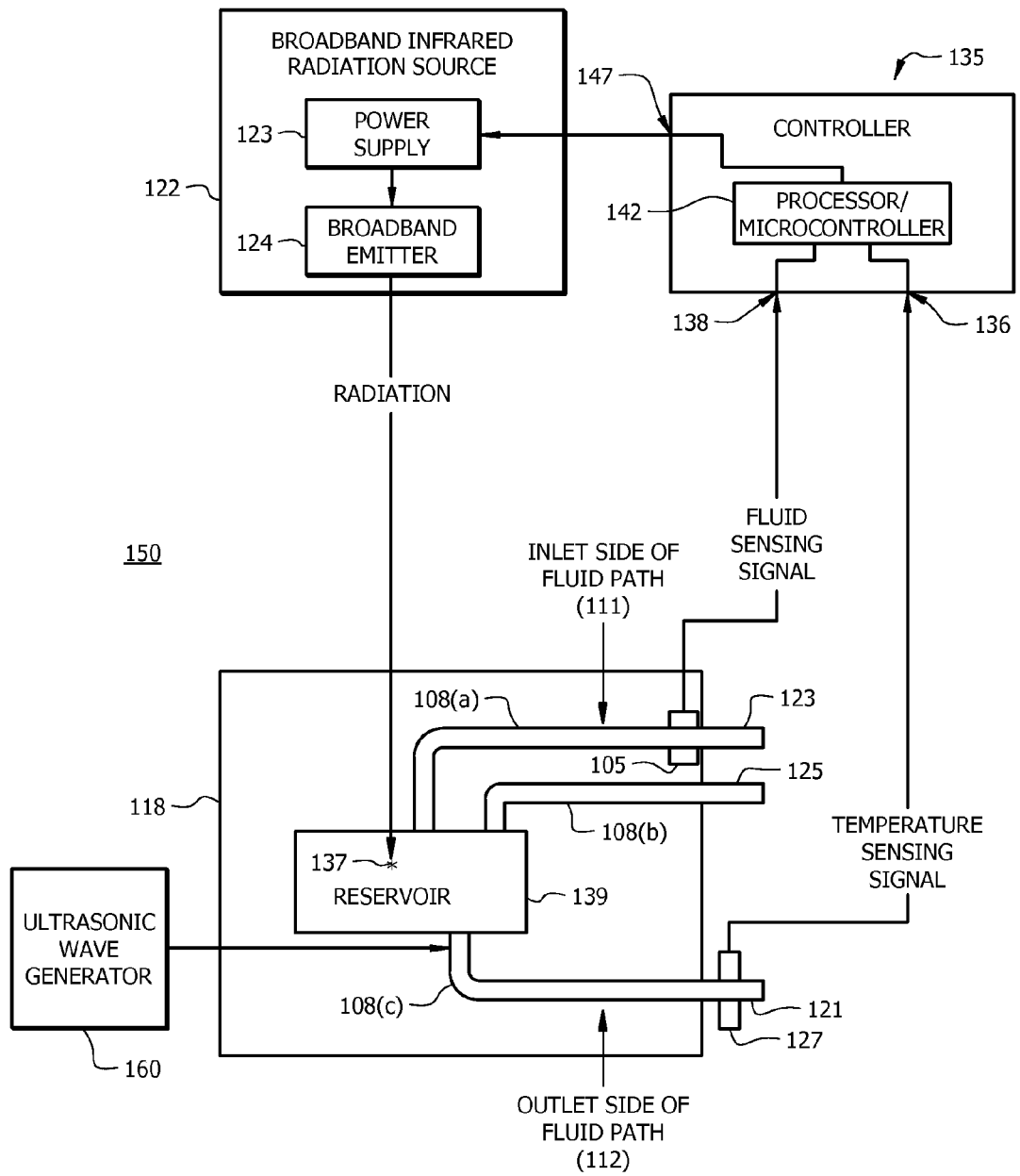
FIG. 1B illustrates a schematic of a system for heating a medical fluid comprising a flow turbulence enhancing structure comprising an ultrasonic wave generator for mixing the heated medical fluid and at least one fluid detector for sensing the medical fluid and shutting off the radiation source when an insufficient flow is detected, according to a disclosed embodiment.

FIG. 1B illustrates a schematic of a system 150 for heating a medical fluid comprising a container and at least one broadband infrared radiation source for heating a medical fluid while in the container, and an active flow turbulence enhancing structure comprising an ultrasonic wave generator 160 for mixing the heated medical fluid, and at least one fluid detector for sensing the medical fluid and shutting off the radiation source 122 when an insufficient flow is detected, according to a disclosed embodiment. System 150 is equivalent to system 100 shown in FIG. 1A except ultrasonic wave generator 160 shown in FIG. 1B replaces the plurality of flow obstacles 141.

Figure 1C:
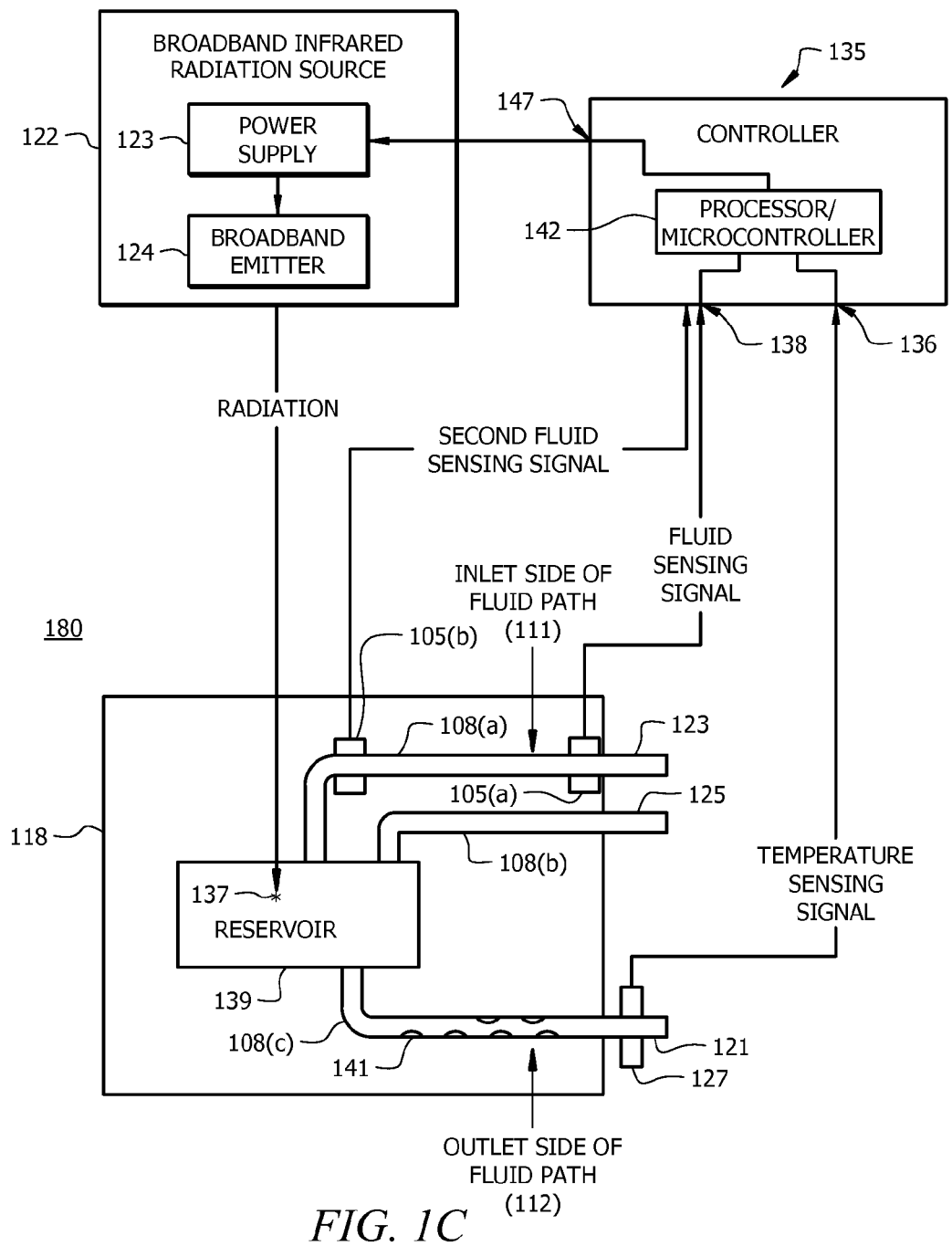
FIG. 1C illustrates a schematic of a system for heating a medical fluid comprising a first and a second fluid detector spaced apart from one another, according to a disclosed embodiment.

If only one fluid detector 105 is included in the system, it can generally only detect the presence and absence of the medical fluid. FIG. 1C illustrates a schematic of a system 180 for heating a medical fluid comprising a container and at least one broadband infrared radiation source for heating a medical fluid while in the container, and a first and a second fluid detector 105(*a*) and 105(*b*) spaced apart from one another to allow calculation of the flow rate of the medical fluid, according to a disclosed embodiment. The first fluid detector 105(*a*) is for generating a first fluid sensing signal the second fluid detector 105(*b*) is for generating a second fluid sensing signal. The processor or microcontroller 142 in controller 135 is coupled to receive both the first and second fluid sensing signals, and to calculate a flow rate of the medical fluid using the first and second fluid sensing signals. When the two fluid detectors with a known separation distance are provided, the Inventor has recognized they can provide information which when taken together can be used to detect the flow rate. For example, by knowing the inner diameter of fluid path portion 108(*a*), when the flow wave flows through the region interrogated by first fluid detector 105(*a*), it can generate a flow sensing signal within a few microseconds. The flow wave then triggers the second fluid detector 105(*b*) after the wave passes the second fluid detector 105(*b*). By calculating the time difference of arrival, the flow rate of medical fluid can be calculated. Based on the flow rate, the power applied to the radiation source 122 by power supply 123 can be controlled to heat the medical fluid to maintain the medical fluid in a predetermined temperature range.

Figure 2:
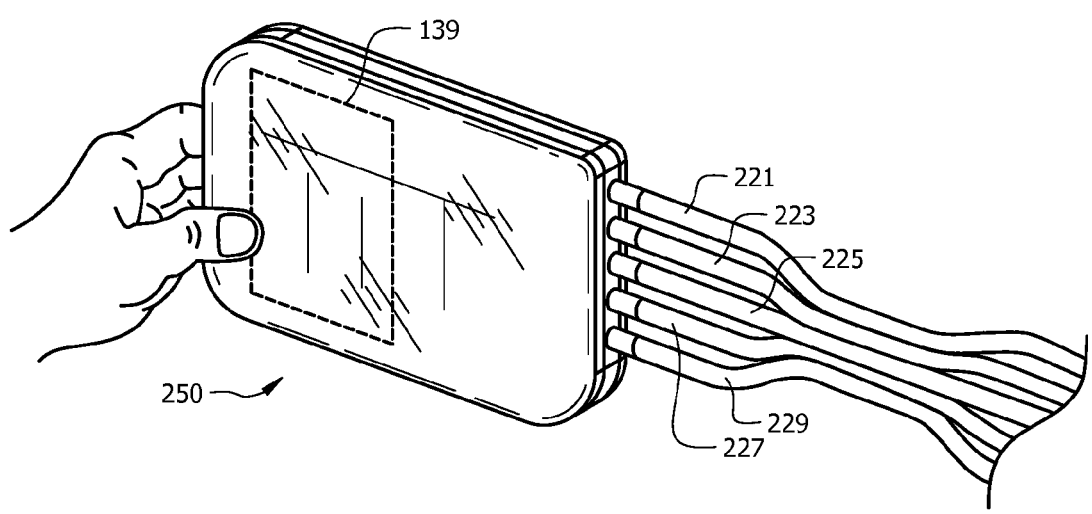
FIG. 2 illustrates a schematic of a system for heating a medical fluid comprising a dedicated container comprising an inlet tube and an outlet tube including and at least one broadband infrared radiation source for heating a medical fluid while in the container, according to a disclosed embodiment.
Figure 2:
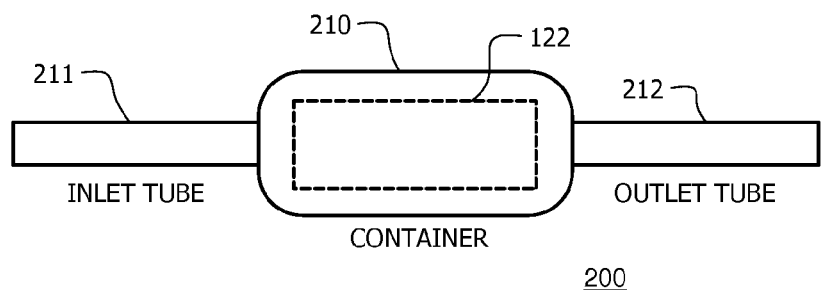

As described above, in another disclosed embodiment the system for heating medical fluid is in the form of a dedicated container for heating the medical fluid, and is thus separate from the dialysis machine. FIG. 2 illustrates a schematic of a system 200 for heating a medical fluid comprising a dedicated container 210 comprising an inlet tube 211 and an outlet tube 212 including and at least one broadband infrared radiation source 132 for heating a medical fluid while in the container 210, according to a disclosed embodiment. Container 210 can be based on system 100 comprising container 118 shown in FIG. 1A or system 150 comprising container 118 shown in FIG. 1B, and can be modified to have a single inlet. Container 210 can be connected a cartridge, such as cartridge 250, also shown in FIG. 2. Container 210 can be connected to an inlet of the cartridge (221, 223, 225 or 227) or the outlet 229 of the cartridge 250. In this arrangement, the existing design of the cartridge 250 need not be changed.

Figure 3:
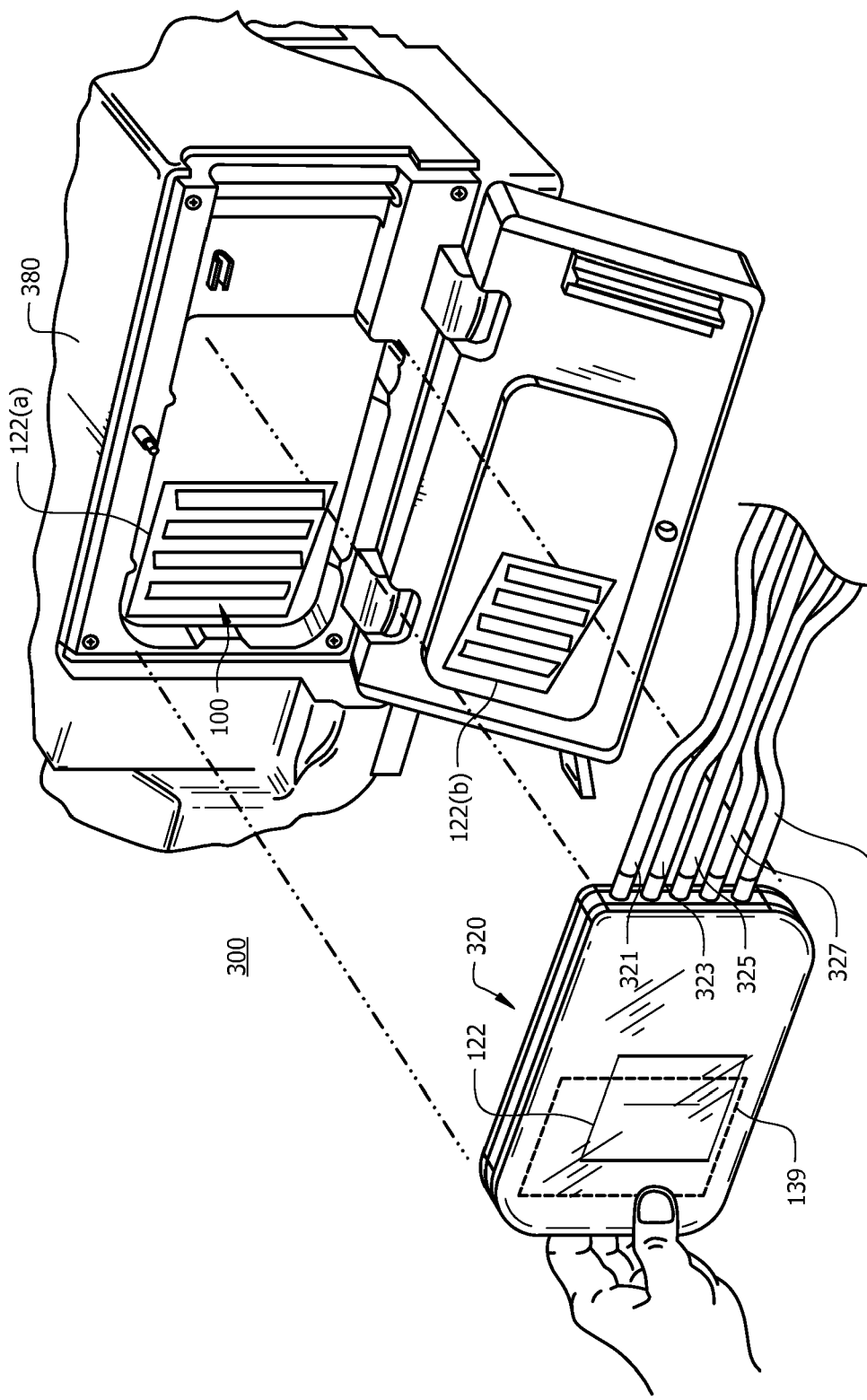
FIG. 3 illustrates a partially exploded schematic view of a system for heating a medical fluid comprising a cartridge positioned within a housing including at least one cartridge inlet and a cartridge outlet, according to a disclosed embodiment.

As described above, in another disclosed embodiment, the broadband infrared radiation source is placed (e.g., mounted) within a dialysis machine including a housing. FIG. 3 illustrates a partially exploded schematic view of a system 300 for heating a medical fluid comprising a cartridge 320 positioned within a housing 380 including at least one cartridge inlet 321, 323, 325, and 327 shown, and a cartridge outlet 329, wherein the cartridge 320 comprises a reservoir 139 in the fluid path, according to a disclosed embodiment. Based on the broadband infrared source power available and the maximum flow rate of the medical fluid to be heated, either a single broadband infrared radiation source is aligned at one side of the cartridge 320 or a pair of broadband infrared radiation sources can be aligned at both sides of the cartridge 320. System 300 shown in FIG. 3 includes a multi-emitter first broadband infrared radiation source 122(*a*) and second multi-emitter broadband infrared radiation source 122(*b*) positioned in the region between the fluid path and the housing 380 on opposing sides of the cartridge 320. In system 300, the medical fluid is heated while in the reservoir 139.

Figure 4:
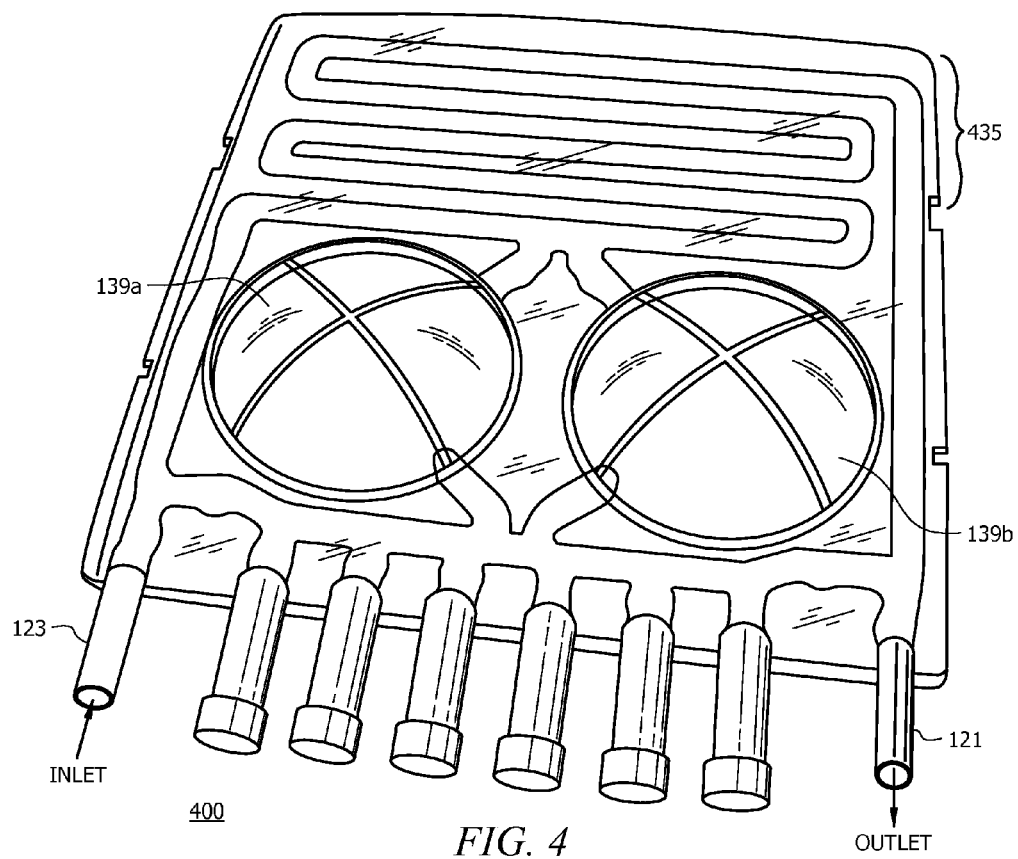
FIG. 4 illustrates a cartridge having a fluid path that comprises an extended flow area portion after the reservoirs, according to a disclosed embodiment.

FIG. 4 illustrates a cartridge 400 having a fluid path that comprises an extended flow area portion 435 after reservoirs 139(a) and 139(b), according to a disclosed embodiment. The extended flow area portion 435 is positioned between the reservoirs 139(a) and 139(b) and the cartridge outlet 121. The extended flow area portion can provide at least 60% of the total length the fluid path. In one embodiment the focus location provided by the broadband infrared radiation source(s) is within the extended flow area portion 435.

A method for heating a medical fluid according to a disclosed embodiment comprises flowing the medical fluid into a fluid path within a container having an inlet an outlet, heating the medical fluid by directing broadband infrared radiation having a focus location within the fluid path to provide a heated medical fluid, and mixing the heated medical fluid using flow turbulence in the fluid path or proximate to the outlet for increasing a temperature uniformity of the heated medical fluid. As used herein, "proximate to the outlet" is defined to be a distance that is within 20 mm, generally being within 10 mm. The medical fluid can comprise a peritoneal dialysis fluid. The method can further comprise sensing a presence of the medical fluid or the heated medical fluid in the fluid path and generating a fluid sensing signal, and controlling the heating of the medical fluid by emitting the broadband infrared radiation only while the fluid sensing signal indicates the medical fluid is present in the container. The method can also comprise calculating a flow rate of the medical fluid, and based on the flow rate, determining a time to initiate the heating. The method can further comprise after the mixing, measuring a temperature of the heated medical fluid and generating a temperature sensing signal, and controlling the heating based on the temperature sensing signal to maintain the heated medical fluid in a predetermined temperature range.

Figure 5:
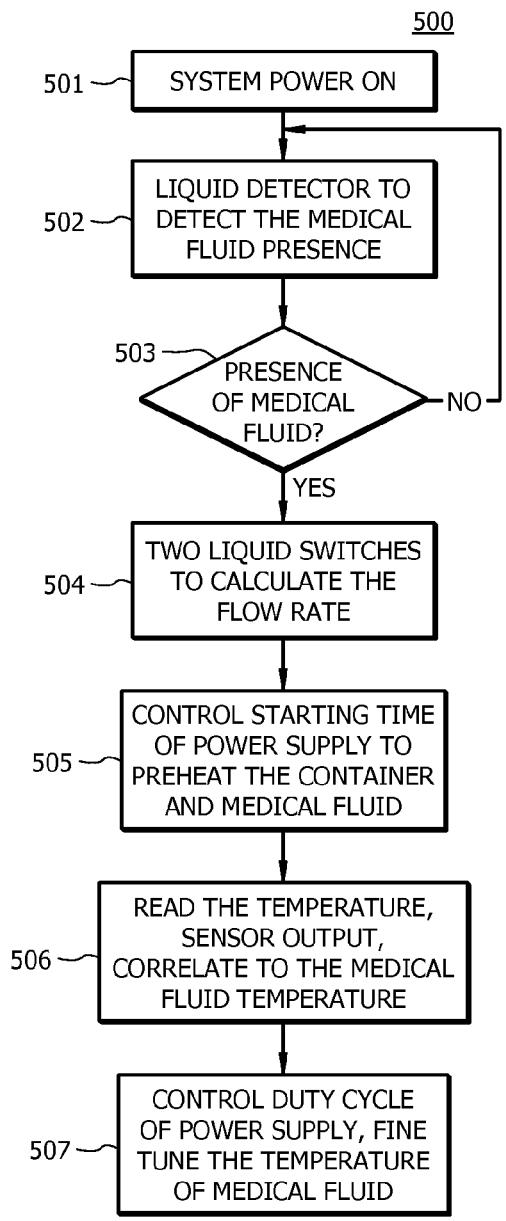
FIG. 5 shows steps in an exemplary control algorithm for heating a medical fluid while preventing melting or burning of the container material and for controlling the temperature of the heated medical fluid, according to a disclosed embodiment.

FIG. 5 shows steps in an exemplary control algorithm 500 for heating a medical fluid while preventing melting or burning of the container material and for controlling the temperature of the heated medical fluid, according to a disclosed embodiment. Step 501 begins method 500 with the system power being turned on. In step 502 a liquid switch (e.g., optical switch) detects whether the medical fluid is present in the container. Step 503 is a decision block wherein if the medical fluid is determined to not be present in the container, the method returns to step 502, while if the medical fluid is determined to be present in the container the method advances to step 504. Step 504 comprises using two spaced apart fluid detectors as described above to calculate the flow rate of the medical fluid. In step 505, the flow rate information is used to control the starting time of the power supply to begin heating the container (e.g., cartridge) and the medical fluid therein. Step 506 comprises obtaining as fluid temperature reading from the heated medical fluid by correlating the temperature sensor output to the temperature of the heated medical fluid. Step 507 comprises controlling the power output of the power supplied associated with the broadband emitter based on the fluid temperature reading to maintain the heated medical fluid in a desired temperature range (typically 37 to 39° C.). In one embodiment the power supply is a pulse width modulated (PWM) power supply and the duty cycle of the PWM power supply is modulated to maintain the heated medical fluid in a desired temperature range.

Figure 6A:
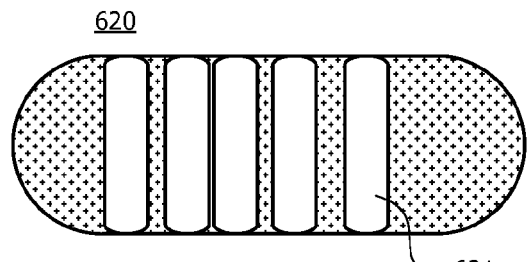
FIGS. 6A and 6B show cross-sectional depictions of exemplary fluid path portions having flow obstacle arrangements therein, according to disclosed embodiments.
Figure 6B:
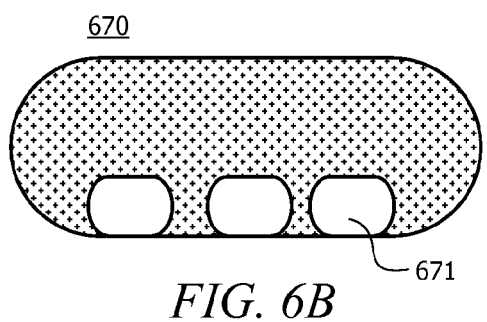

FIGS. 6A and 6B show cross-sectional depictions of exemplary fluid path portions having flow obstacle arrangements therein. FIG. 6A shows a fluid path portion 620 including a plurality of bars 621 within its inner walls. Bars 621 can be molded along the fluid path of container or cartridge during manufacturing. FIG. 6B shows a fluid path portion 670 including a surface bumps 671 protruding from its inner walls.

Advantages of disclosed embodiments may include one or more of the following. Price may be comparable or less than conventional medical fluid heaters. The size may be smaller. Moreover, performance improvements through the disclosed flow turbulence enhancing structure for mixing the heated medical fluid, and reliability improvements including flow detection of the medical fluid to control the triggering of the broadband infrared radiation source and the algorithm disclosed to avoid melting or the burning of fluid container (such as the cartridge), are all significant advantages for medical fluid heaters disclosed herein.

While various disclosed embodiments have been described above, it should be understood that they have been presented by way of example only, and not limitation. Numerous changes to the disclosed embodiments can be made in accordance with the disclosure herein without departing from the spirit or scope of this application. Thus, the breadth and scope of the disclosed embodiments should not be limited by any of the above described embodiments. Rather, the scope of the disclosed embodiments should be defined in accordance with the following claims and their equivalents.

Although the disclosed embodiments have been illustrated and described with respect to one or more implementations, equivalent alterations and modifications will occur to others skilled in the art upon the reading and understanding of this specification and the annexed drawings. In addition, while a particular feature may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this application belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

The invention claimed is:

1. A system for heating a medical fluid, comprising:
 a container having at least one inlet for receiving said medical fluid and at least one outlet for delivering said medical fluid, and a fluid path within said container having an inlet side coupled to said inlet and an outlet side coupled to said outlet;
 at least one broadband infrared radiation source comprising a power supply coupled to a broadband emitter for emitting infrared radiation, said broadband emitter positioned to provide a focal location within said fluid path to heat said medical fluid to generate a heated medical fluid;

a flow turbulence enhancing structure for mixing said heated medical fluid;

at least one fluid detector for sensing a presence of said medical fluid in said fluid path and for generating a fluid sensing signal, and a controller having an input coupled to receive said fluid sensing signal and an output that is coupled to said power supply, said controller for controlling a power output of said power supply based on said fluid sensing signal indicating a presence of said medical fluid in said container.

2. The system of claim 1, wherein said flow turbulence enhancing structure comprises a plurality of flow obstacles protruding from inner walls of said fluid path and positioned downstream from said focal location to provide an obstruction of between 20% and 50% of a cross-sectional area of a portion of said fluid path having said plurality of flow obstacles.

3. The system of claim 1, wherein said flow turbulence enhancing structure comprises an ultrasonic wave generator.

4. The system of claim 1, wherein said flow turbulence enhancing structure mixes said heated medical fluid in said fluid path to increase a temperature uniformity of said heated medical fluid provided at said outlet.

5. The system of claim 4, wherein said flow turbulence enhancing structure comprises a plurality of flow obstacles protruding from inner walls of said fluid path and positioned downstream from said focal location to provide an obstruction of between 20% and 50% of a cross-sectional area of a portion of said fluid path having said plurality of flow obstacles.

6. The system of claim 4, wherein said flow turbulence enhancing structure comprises an ultrasonic wave generator.

7. The system of claim 1, wherein said controller controls a power output of said power supply so that said broadband infrared radiation source is switched on only when said fluid sensing signal indicates said medical fluid is present in said container.

8. The system of claim 1, wherein said fluid detector comprises an ultrasonic, optical transmissive, or optical reflective-based fluid detector.

9. The system of claim 1, further comprising a temperature sensor for measuring a temperature of said heated medical fluid and generating a temperature sensing signal, said temperature sensing signal coupled to said controller, wherein said controller controls said power output based on said temperature sensing signal to maintain said heated medical fluid in a predetermined temperature range.

10. The system of claim 1, wherein said at least one fluid detector comprises a first fluid detector for generating a first fluid sensing signal, a second fluid detector for generating a second fluid sensing signal, and wherein said controller comprises a processor coupled to receive said first and said second fluid sensing signals, said processor calculating a flow rate of said medical fluid using said first and said second fluid sensing signals.

11. The system of claim 1, wherein said broadband infrared radiation source provides a peak wavelength $\geq 2$ microns, and said container material provides $\geq 80\%$ average transmission in a wavelength range from 2 to 4 microns.

12. The system of claim 1, wherein said at least one broadband infrared radiation source comprises a first and a second broadband infrared radiation source, and wherein said container is positioned between said first and said second broadband infrared radiation source.

13. The system of claim 1, further comprising a cartridge having a cartridge inlet and a cartridge outlet, and a reservoir between said cartridge inlet and said cartridge outlet, wherein said outlet is coupled to said cartridge inlet or said inlet is coupled to said cartridge outlet.

14. The system of claim 1, further comprising a dialysis machine including a housing, wherein said container comprises a cartridge positioned within said housing and said inlet comprises a cartridge inlet and said outlet comprises a cartridge outlet, said cartridge comprising a reservoir in said fluid path, wherein said broadband infrared radiation source is positioned between said fluid path and said housing.

15. The system of claim 14, wherein said fluid path comprises an extended flow area portion positioned between said reservoir and said cartridge outlet, said extended flow area portion providing at least 60% of a total length of said fluid path.

16. The system of claim 15, wherein said focus location is within said reservoir or said extended flow area portion.

17. A method for heating a medical fluid, comprising:
receiving, with at least one inlet of a container, said medical fluid, said container having at least one outlet for delivering said medical fluid and a fluid path within said container having an inlet side coupled to said inlet and an outlet side coupled to said outlet;

heating said medical fluid to generate a heated medical fluid by emitting infrared radiation with a broadband emitter of at least one broadband infrared radiation source, said at least one broadband infrared radiation source comprising a power supply coupled to said broadband emitter, said broadband emitter positioned to provide a focal location within said fluid path to generate said heated medical fluid;

mixing said heated medical fluid with a flow turbulence enhancing structure;

sensing, with at least one fluid detector, a presence of said medical fluid in said fluid path;

generating, with said at least one fluid detector, a fluid sensing signal;

receiving, with an input of a controller, said fluid sensing signal, an output of said controller coupled to said power supply;

controlling, with said controller, a power output of said power supply based on said fluid sensing signal indicating a presence of said medical fluid in said container.

18. The method of claim 17, wherein controlling, with said controller, said power output of said power supply comprises:
controlling said heating by emitting said infrared radiation only while said fluid sensing signal indicates said medical fluid is present in said container.

19. The method of claim 18, further comprising:
calculating a flow rate of said medical fluid, and
based on said flow rate, determining a time to initiate said heating.

20. The method of claim 17, further comprising:
after said mixing, measuring a temperature of said heated medical fluid and generating a temperature sensing signal; and controlling said heating based on said temperature sensing signal to maintain said heated medical fluid in a predetermined temperature range.

21. The method of claim 20, wherein said medical fluid comprises a peritoneal dialysis fluid.

22. The system of claim 1, wherein said broadband emitter comprises a blackbody infrared source.

* * * * *